(12) United States Patent
Rajbhandary et al.

(10) Patent No.: US 6,964,859 B2
(45) Date of Patent: Nov. 15, 2005

(54) SUPPRESSOR TRNA SYSTEM

(75) Inventors: Uttam L. Rajbhandary, Lexington, MA (US); Caroline Koehrer, Mils (AT)

(73) Assignee: Massachusetts Institute of Technology, Cambridge, MA (US)

(*) Notice: Subject to any disclaimer, the term of this patent is extended or adjusted under 35 U.S.C. 154(b) by 173 days.

(21) Appl. No.: 10/271,453

(22) Filed: Oct. 16, 2002

(65) Prior Publication Data

US 2003/0224479 A1 Dec. 4, 2003

Related U.S. Application Data

(60) Provisional application No. 60/329,702, filed on Oct. 16, 2001.

(51) Int. Cl.$^7$ .......................... C12P 21/02; C12N 5/06; C12N 5/10
(52) U.S. Cl. ...................................... 435/70.3; 435/325
(58) Field of Search ............................. 435/70.3, 325, 435/458, 455, 461, 371; 536/23.1; 514/44

(56) References Cited

U.S. PATENT DOCUMENTS

| | | | |
|---|---|---|---|
| 6,309,830 B1 * | 10/2001 | Panchal et al. | ................ 435/6 |
| 2003/0082575 A1 | 5/2003 | Schultz et al. | |
| 2003/0108885 A1 | 6/2003 | Schultz et al. | |

OTHER PUBLICATIONS

Verma IM et al., Gene therapy—promises, problems and prospects, Nature, 389(6648):239–42, 1997.*
Palu G et al., In pursuit of new developments for gene therapy of human diseases, J Biotechnol., 68(1):1–13, 1999.*
Luo D et al., Synthetic DNA delivery systems, Nat Biotechnol., 18(1):33–7, 2000.*

Anderson, et al., "Fluorescence Resonance Energy Transfer Between Unnatural Amino Acids in a Structurally Modified Dihydrofolate Reductase", *J. Am. Chem. Soc.* 124: 9674–9675, 2002.
Atkinson, et al., "Mutations to Nonsense Codons in Human Genetic Disease: Implications for Gene Therapy by Nonsense Suppressor tRNAs", *Nucleic Acids Res.* 22: 1327–1334, 1994.
Bain, et al., "Ribosome–Mediated Incorporation of a Non–Standard Amino Acid into a Peptide Through Expansion of the Genetic Code", *Nature*, 356: 537–539, 1992.
Bain, et al., Biosynthetic Site–Specific Incorporation of a Non–Natural Amino Acid into a Polypeptide, *J. Am. Chem. Soc.*, 111: 8013–8014, 1989.
Bain, et al., "Site–Specific Incorporation of Unnatural Residues During in Vitro Protein Biosynthesis with Semisynthetic Aminoacyl–tRNAs", *Biochemistry*, 30: 5411–5421, 1991.
Baldini, et al., "Mischarging *Escherichia coli* tRNA$^{Phe}$ with L–4'–[3–(Trifluoromethyl)–3H–Diazirin –3–yl] Phenylalanine, a Photoactivatable Analogue of Phenylalanine" *Biochemistry*, 27: 7951–7959, 1988.
Barton–Davis, et al., "Aminoglycoside Antibodies Restore of Dystrophin Function to Skeletal Muscles of Mdx Mice" *J. Clin. Invest.* 104: 375–381, 1999.

(Continued)

*Primary Examiner*—Terry McKelvey
*Assistant Examiner*—Jennifer Dunston
(74) *Attorney, Agent, or Firm*—Choate, Hall & Stewart

(57) ABSTRACT

The present invention provides techniques and reagents for read-through of stop codons in mammalian cells. In certain embodiments, the invention provides methods in which a mammalian cell is contacted with a synthesized tRNA so that the tRNA is taken up into the cell at levels that allow read-through of stop codons. Preferably, the synthesized suppressor tRNA is aminoacylated, optionally with an unnatural amino acid. In certain preferred embodiments, the inventive system is utilized to generate proteins containing two or more unnatural amino acids.

10 Claims, 9 Drawing Sheets

OTHER PUBLICATIONS

Buvoli, et al., "Suppressin of Nonsense Mutations in Cell Culture and Mice by Multimerized Suppressor tRNA Genes", *Mol. Cell. Biol.* 20: 3116–3124, 2000.

Suppressor tRNA Genes, *Mol. Cell. Biol.* 20: 3116–3124, 2000.

Capone, et al., "Introduction of UAG, UAA, and UGA Nonsense Mutations at a Specific Site in the *Escherichia coli* Chloramphenicol Acetyl–Transferase Gene: Use in Measurement of Amber, Ochre, and Opal Suppression in Mammalian Cells" *Mol. Cell. Biol.* 6: 3059–3067, 1986.

Chin, et al., "Addition of p–Azido–L–Phenylalanine to the Genetic Code of *Escherichia coli*", *J. Am. Chem. Soc.* 124: 9026–9027, 2002.

Chow, et al., "Saccharomyces Cerevisiae Cytoplasmic Tyrosyl–tRNA Synthetase Gene", *J. Biol. Chem.* 268: 12855–12863, 1993.

Clark, et al., "Tyrosine Activation and Transfer to Soluble Ribonucleic Acid" *J. Biol. Chem.* 237: 3698–3702, 1962.

Cload, et al., "Development of Improved tRNAs for in Vitro Biosynthesis of Proteins Containing Unnatural Amino Acids", *Chem. Biol.* 3: 1033–1038, 1996.

Doctor, et al., "Species Specificity of Amino Acid Acceptor Ribonucleic Acid and Aminoacyl Soluble Ribonucleic Acid Synthetases", *J. Biol. Chem.* 238: 3677–3681, 1963.

Drabkin, et al., "Initiator–Elongator Discrimination in Vertebrate tRNAs for Protein Synthesis", *Mol. Cell. Biol.*, 18: 1459–1466, 1998.

Drabkin, et al., "Amber Suppression in Mammalian Cells Dependent Upon Expression of an *Escherichia coli* Aminoacyl–tRNA Synthetase Gene", *Mol. Cell. Biol.* 16: 907–913, 1996.

Edwards, et al., "A Bacterial Amber Suppressor in Saccharomyces Cerevisiae Is Selectively Recognized by a Bacterial Aminoacyl–tRNA Synthetase", *Mol. Cell. Biol.* 10: 1633–1641, 1990.

Elbashir, et al., "Duplexes of 21–Nucleotide RNAs Mediate RNA Interference in Cultured Mammalian Cells", *Nature (London)*, 411: 494–498, 2001.

Heckler, et al., "T4 RNA Ligase Mediated Preparation of Novel "Chemically Misacylated" tRNAs$^{Phe}$", *Biochemistry*, 23: 1468–1473, 1984.

Hirao, et al., "An Unnatural Base Pair for Incorporating Amino Acid Analogs into Proteins", *Nat. Biotechnol.* 20: 177–182, 2002.

Hofman, et al., "Fluorescent Monitoring of Kinase Activity in Real Time: Aevelopment of a Robust Fluorescence–Based Assay for Abl Tyrosine Kinase Activity", *Bioorg. Med. Chem. Lett.*, 11: 3091–3094, 2001.

Hohsaka, et al., "Incorporation of Two Different Nonnatural Amino Acids Independently into a Single Protein Through Extension of the Genetic Code", *J. Am. Chem. Soc.* 121: 12194–12195, 1999.

Hohsaka, et al., "Incorporation of Nonnatural Amino Acids into Streptavidin Through in Vitro Frame–Shift Suppression", *J. Am. Chem. Soc.*, 118: 9778–9779, 1996.

Hohsaka, et al., "Five–Base Condons for Incorporation of Nonnatural Amino Acids into Proteins", *Nucleic Acids Res.* 29: 3646–3651, 2001.

Ilegems, et al., Monitoring Mis–acylated tRNA Suppression Efficiency in Mammalian Cells via EGFP Fluorescence Recovery, *Nucleic Acids Res.* 30(23): 1–6, 2002.

Kim, et al., "A Highly Efficient Cell–Free Protein Synthesis System from *Escherichia coli*", *Eur. J. Biochem.*, 239: 881–886, 1996.

Kleinschmidt, et al., "RNA Processing and Ribonucleoprotein Assembly Studied in Vivo by RNA Transfection" *Proc. Natl. Acad.Sci, USA*, 87: 1283–1287, 1990.

Kohrer, "Import of Amber and Ochre Suppressor tRNAs into Mammalian Cells: A general Approach to Site–Specific Insertion of Amino Acid Analogues into Proteins", *Proc. Natl. Acad. Sci. USA*, 98: 14310–14315, 2001.

Kowal, et al., "Twenty–First Aminoacyl–tRNA Synthetase–Suppressor tRNA Pairs for Possible Use in Site–Specific Incorporation of Amino Acid Analogues into Proteins in Eukaryotes and in Eubacteria" *Proc. Natl. Acad. Sci. USA*, 98: 2268–2273, 2001.

Kurokawa, et al., "A Pair of Flurescent Resonance Energy Transfer–Based Probes for Tyrosine Phosphorylation of the Crkil Adaptor Protein in Vivo", *J. Biol. Chem.*, 276: 31305–31310, 2001.

Kwon, et al., "Breaking the Degeneracy of the Genetic Code", *J. Am. Chem. Soc.* 125: 7512–7513, 2003.

Laski, et al., "Synthesis of an Ochure Suppressor tRNA Gene and Expression in Mammalian Cells", *EMBO, J*3: 2445–2452, 1984.

Lee, et al., "Mutants of *Escherichia coli* Initiator tRNA that Suppress Amber Codons in Saccharomyces Cerevisiae and are Aminoacylated with Tyrosine by Yeast Extracts", *Proc. Natl. Acad. Sci. USA*, 88: 11378–11382, 1991.

Liu, et al., "Progress Toward the Evolution of an Organism with an Expanded Genetic Code", *Proc. Natl. Acad. Sci. USA*, 96: 4780–4785, 1999.

Liu, et al., "Engineering a tRNA and Aminoacyl–tRNA Synthetase for the Site–Specific Incorporation of Unnatural Amino Acids into Proteins in Vivo", *Proc.Natl. Acad. Sci. USA*, 94: 10092–10097, 1997.

Lu, et al., "Site–Specific Incorporation of a Phosphotyrosine Mimetic Reveals a Role for Tyrosine Phosphorylation of SHP–2 in Cell Signaling", Mol. Cell, 8: 759–769, 2001.

Malone, et al., "Cationic Liposome–Mediated RNA Transfection", *Proc. Natl. Acad. Sci. USA*, 86: 6077–6081, 1989.

Mamaev, et al., "Firefly Luciferase: Alteration of the Color of Emitted Light Resulting from Substitution at Position 286", *J. Am. Chem. Soc.* 118: 7243–7244, 1996.

Mangroo, et al., "An Anticodon Sequence Mutant of *Escherichia coli* Initiator tRNA: Possible Importance of a Newly Acquired Base Modification Next to the Anticodon on Its Activity in Initiation" *J. Bacteriol.* 177: 2858–2862, 1995.

Monahan, et al., "Site–Specific Incorporation of Unnatural Amino Acids into Receptors Expressed in Mammalian Cells", *Chem. Biol.* 10: 573–580, 2003.

Moore, et al., "Quadruplet Codons: Implications for Code Expansion and the Specification of Translation Step Size",*J. Mol. Biol.* 298: 195–209, 2000.

Translation Step Size, *J. Mol. Biol.* 298: 195–209, 2000.

Negrutskii, et al., "Channeling of Aminoacyl–tRNA for Protein Synthesis in vivo", *Proc. Natl Acad. Sci, USA*, 88: 4491–4995, 1991.

Negrutskii, et al., "Supramolecular Organization of the Mammalian Translation System",*Proc. Natl. Acad. Sci. USA*, 91: 964–968, 1994.

Noren, et al., "A General Method for Site–Specific Incorporation of Unnatural Amino Acids into Proteins" *Science*, 244: 182–188, 1989.

Nowak, et al., "Nicotinic Receptor Binding Site Probed with Unnatural Amino Acid Incorporation in Intact Cells", *Science*, 268: 439–442, 1995.

Panchal, et al., "Partial Functional Correction of Xeroderma Pigmentosum Group A Cells by Suppressor tRNA", *Hum. Gene Ther*. 10: 2209–2219, 1999.

Sakamoto, et al., "Site–Specific Incorporation of an Unnatural Amino Acid into Proteins in Mammalian Cells", *Nucleic Acids Res*. 30: 4692–4699, 2002.

Seong, et al., "Suppression of Amber Codons in Vivo as Evidence That Mutants Derived from *Escherichia coli* Initiator tRNA Can Act at the Step of Elongation in Protein Synthesis" *J. Biol.Chem*. 264: 6504–6508, 1989.

Temple, et al., "Construction of a Functional Human Suppressor tRNA Gene: an Approach to Gene Therapy for β–Thalassaemia" *Nature, (London)*, 296: 537–540, 1982.

Ting, et al., "Genetically Encoded Fluorescent Reporters of Protein Tyrosine Kinase Activities in Living Cells", *Proc. Natl. Acad. Sci.USA*, 98: 15003–15008, 2001.

Wakasugi, et al., "Genetic Code in Evolution: Switching Species–Specific Aminoacylation with a Peptide Transplant", *EMBO, J*. 17: 297–305, 1998.

Wang, et al., "A New Functional Suppressor tRNA/Aminoacyl–tRNA Synthetase Pair for the in Vivo Incorporation of Unnatural Amino Acids into Proteins", *J. Am. Chem. Soc*. 122: 5010–5011, 2000.

Wang, et al., "Adding L–3–(2–Naphthyl)Alanine to the Genetic Code of *E. coli*", *J. Am. Chem. Soc*. 124: 1836–1837, 2002.

Wang, et al., "Expanding the Genetic Code of *Escherichia coli*" *Science*, 292: 498–500, 2001.

Yu, et al., "Essential Regions of the tRNA Primer Required for HIV–1 Infectivity", *Nucleic Acids Res*. 28: 4783–4789, 2000.

Zhang, et al., "Genetically Encoded Reporters of Protein Kinase A Activity Reveal Impact of Substrate Tethering", *Proc. Natl. Acad. Sci. USA*, 98: 14997–15002, 2001.

* cited by examiner

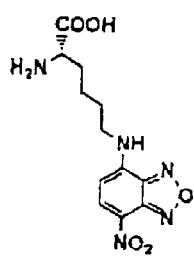
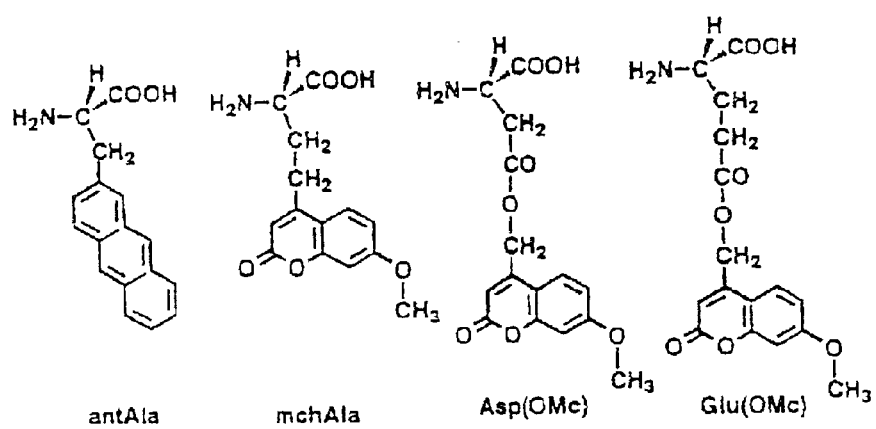
FIGURE 6-A

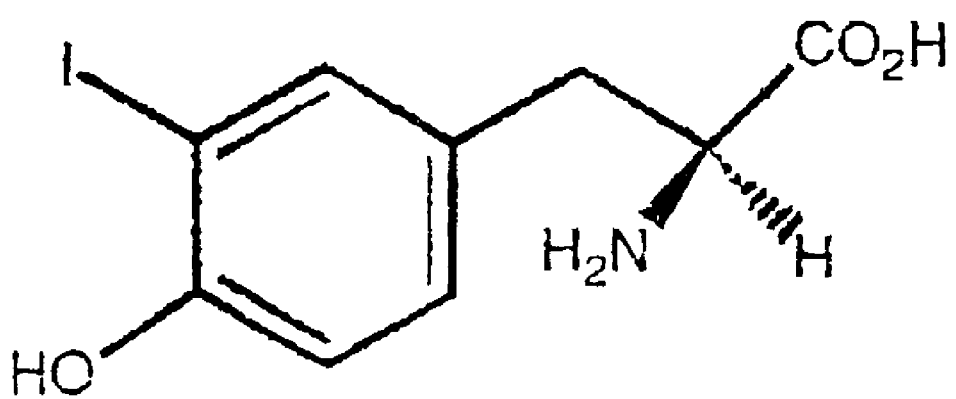
3-iodotyrosine
FIGURE 6-B

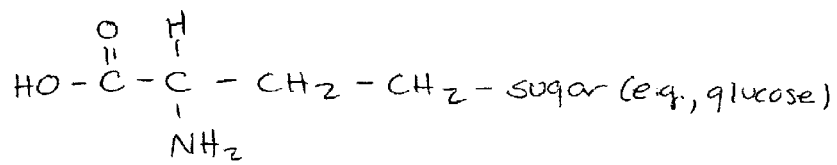
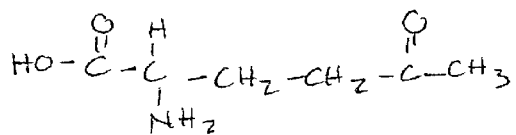
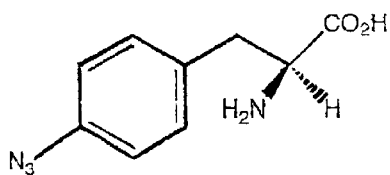
4-azidophenylalanine
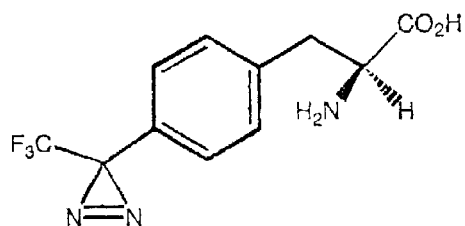
L-4'-[3-(trifluoromethyl)-*3H*-diazirin-3-yl]phenylalanine
[(Tmd)-Phe]
FIGURE 6-C

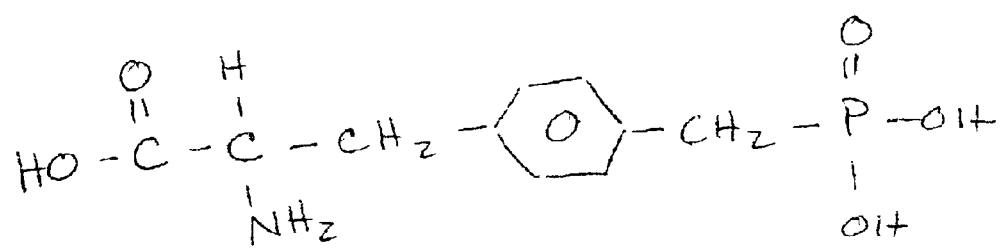
FIGURE 6-D

SUPPRESSOR TRNA SYSTEM

PRIORITY CLAIM

This application claims priority to co-pending U.S. Provisional Application No. 60/329,702, filed Oct. 16, 2001 and pending through Oct. 16, 2002; the entire contents of this priority application are incorporated herein by reference.

BACKGROUND OF THE INVENTION

Significant research effort has been directed toward the development of techniques to introduce unnatural amino acids into polypeptide chains, either by chemical synthesis (see, for example, Hofman et al., *J. Am. Chem. Soc.* 88:5914, 1966), semi-synthetic approaches (see, for example, Borras et al., *Nature* 227:716, 1970; Sealock et al., *Biochemistry* 8:3703, 1969; Inouye et al., *J. Am. Chem. Soc.* 101:752, 1979), modification of reactive side-groups in extant polypeptides (see, for example, Neet et al., *Proc. Natl. Acad. Sci. USA* 56:1606, 1966; Polgar et al., *J. Am. Chem. Soc.* 88:3153, 1966; Kaiser et al., *Science* 266:505, 1984; Mayo et al., *Science* 233:948, 1986), or use of alternatively acylated tRNAs (see, for example, Krieg et al., *Proc. Natl. Acad. Sci. USA* 83:8604, 1986; Wiedmann et al., *Nature* 328:830, 1987; Johnson et al., *Biochemistry* 15:569, 1976; Baldini et al., *Biochemistry* 27:7951, 1988; Roesser et al., *Biochemistry* 25:6361, 1986; Heckler et al., *J. Biol. Chem.* 258:4492, 1983; Noren et al., *Science* 244:182, 1989; Ellman et al., *Met. Enzymol.* 202:301, 1991). Introduction of such unnatural amino acids into proteins allows analysis of protein folding and/or activity, and also allows adjustment of protein characteristics such as solubility, stability, etc.

Unfortunately, most of the techniques available for introducing unnatural amino acids into proteins generate only low protein yields. Furthermore, many techniques can only be utilized in vitro and/or rely or laborious synthetic technologies. Also, those techniques that utilize alternatively acylated tRNAs can typically introduce only a single unnatural amino acid into a given polypeptide chain. There remains a need for the development of more generally applicable systems for introducing unnatural amino acids into proteins. Preferably, such systems should allow unnatural amino acids to be incorporated into growing polypeptide chains in vivo. Alternatively or additionally, such systems should be able to introduce multiple unnatural amino acids into a single protein.

Significant research effort has also been directed at developing techniques and reagents for the treatment or cure of various human genetic diseases. There remains a need for the development of improved systems.

SUMMARY OF THE INVENTION

The present invention provides methods and reagents for reading through stop codons in mammalian cells. In particular, the invention allows suppressor tRNAs that are generated outside of mammalian cells to be introduced into those cells, where they suppress nonsense mutations. In certain embodiments of the invention, the suppressor tRNAs are aminoacylated prior to introduction into the mammalian cells; in other embodiments, they are not aminoacylated prior to introduction. In some preferred embodiments, the tRNAs utilized are not substrates for tRNA synthetases present within the cell. In general, however, when tRNAs are not amioacylated prior to import into cells, it is preferred that the tRNAs are substrates for endogenous tRNA synthetases The techniques and reagents of the present invention may be utilized to introduce one or more unnatural amino acids into polypeptides synthesized in mammalian cells; in certain embodiments such polypeptides may contain at least two or more unnatural amino acids. Alternatively or additionally, inventive methods and/or reagents may be utilized to read through stop codons responsible for a disease phenotype in a mammalian cell.

DEFINITIONS

Disease state: For the purposes of the present invention, a "disease state" or "disease phenotype" is a characteristic of a mammalian cell that results from a stop codon within the coding region of a gene inside the cell (e.g., that results from a nonsense mutation). For example, an increasing number of human genetic diseases are thought to be caused by nonsense mutations (see, for example, Atkinson et al., *Nuc. Acids Res.* 22:1327, 1994). To give but a few examples, β-thalessemia, Duchenne myscular dystrophy, xeroderma pigmentosum, Fanconi's anemia, and cystic fibrosis can all be caused by nonsense mutations in identified genes.

Endogenous tRNA synthetase: A tRNA synthetase is considered to be "endogenous" to a cell if it is present in the cell into which a tRNA is introduced according to the present invention. As will be the apparent to those of ordinary skill in the art, a tRNA synthetase may be considered to be endogenous for these purposes whether it is naturally found in cells of the relevant type, or whether the particular cell at issue has been engineered or otherwise manipulated by the hand of man to contain or express it.

Suppressor tRNA: A "suppressor tRNA" is one whose anti-codon is complementary with a codon that would otherwise terminate translation, so that detectable read-through occurs under the conditions of the experiment. Standard termination codons are amber (UAG), ochre (UAA), and opal (UGA) codons. However, non-standard termination codons (e.g., 4-nucleotide codons) have also been employed in the literature (see, for example, Moore et al., *J. Mol. Biol.* 298:195, 2000; Hohsaka et al., *J. Am. Chem. Soc.* 121:12194, 1999).

Unnatural amino acid: An "unnatural amino acid" is any amino acid other than the 20 naturally-occurring amino acids, and includes amino acid analogues. In general, any compound that can be incorporated into a polypeptide chain can be an unnatural amino acid. Preferably, such compounds have the chemical structure H—C—COOH.

BRIEF DESCRIPTION OF THE DRAWING

The invention is described with reference to the several Figures of the drawing, in which.

FIG. 6 presents illustrative examples of certain unnatural amino acids that could be incorporated into a protein or polypeptide in accordance with the present invention. FIG. 6A shows certain fluorescent amino acid analogs; FIG. 6B shows an amino acid analog including a heavy atom label (I, which is useful, for instance, in X-ray crystallography; analogs containing F rather than I could be used, for example, for NMR spectroscopy); FIG. 6C shows certain amino acid analogs that include reactive moieties such as photoactivatable groups useful for cross-linking; FIG. 6D depicts a phosphotyrosine analog useful in the practice of the present invention, for example to facilitate the study of cell signalling.

DETAILED DESCRIPTION OF CERTAIN PREFERRED EMBODIMENTS

Transfer RNAs (tRNAs)

Figure 1:
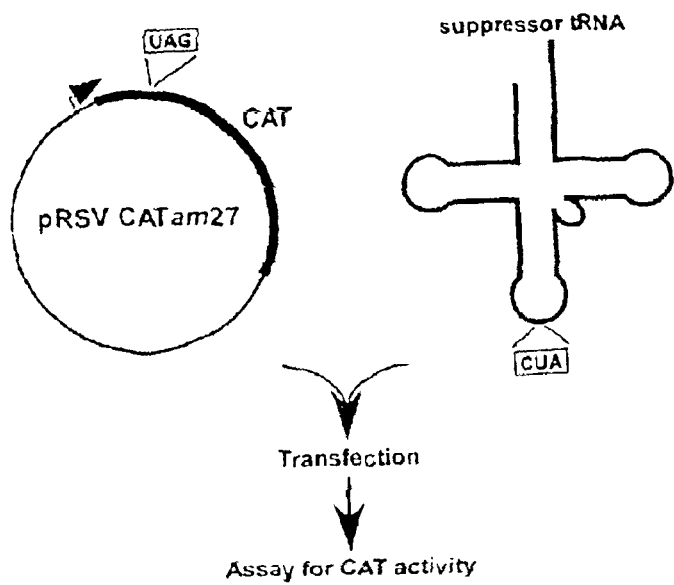
FIG. 1 presents a scheme for assaying import and function of amber suppressor tRNA.

The teachings of the present invention are applicable to any transfer RNA (tRNA) that can be synthesized outside a mammalian cell and subsequently introduced into the cell. As noted herein, certain preferred tRNAs recognize standard nonsense codons. Some preferred tRNAs are aminoacylated prior to import, optionally with an unnatural amino acid. Also, in certain preferred embodiments of the invention, the tRNA employed is not a substrate for any tRNA synthetases present within the cell into which the tRNA is introduced. In such embodiments, when an aminoacylated tRNA is delivered to a cell and contributes its amino acid to a growing polypeptide chain, it cannot be reaminoacylated within the cell. For example, the present invention demonstrates that the E. coli supF tRNA is not a substrate for mammalian tRNA synthetases. In other embodiments of the invention, the tRNA is a substrate for a tRNA synthetase within the cell into which the tRNA is introduced.

Where tRNAs aminoacylated prior to introduction into the cell are utilized, the aminoacyl linkage should preferably be stable under the conditions of transport.

Amino Acids

As mentioned above, in certain embodiments of the invention, tRNAs are aminoacylated prior to being introduced into mammalian cells. Any amino acid or amino acid analog may be utilized to aminoacylate tRNAs in accordance with the present invention. In certain preferred embodiments of the invention, unnatural amino acids are used. For instance, it may be desirable to introduce an unnatural amino acid containing a detectable moiety (e.g., a fluorophore), a photoactivatable group, or a heavy atom (e.g., iodine). Alternatively or additionally, amino acids including chemically reactive moieties could be used. FIG. 6 presents exemplary structures of certain unnatural amino acids that could be used in accordance with the present invention; those of ordinary skill on the art will readily appreciate that any of a variety of other compounds could also be used.

Introducing tRNA into Cells

Any available method may be used in accordance with the present invention to introduced synthesized tRNAs into mammalian cells. In preferred embodiments of the invention, tRNAs are imported into cells using cellular machinery, and are not imposed into the cell lumen by mechanical means such as injection. In general, import processes are characterized by being competable and/or inhibitable. Import offers several advantages over other methods for introducing tRNAs into cells. For example, tRNAs can be imported into multiple cells simultaneously. By contrast, when injection is utilized, (e.g., into xeropus occytes) individual cells must be injected individually. Also, import may achieve higher levels of tRNA within cells, thereby allowing higher levels of production of protein. In particularly preferred embodiments of the invention, tRNAs are introduced into mammalian cells using Effectene or Lipotectamine in conjunction with a nucleic acid condensing enhancer (e.g., DMRIE-C). Without wishing to be bound by any particular theory, we propose that the nuclei acid condensing enhancer renders nucleic acids more compact and therefore easier to import. Such an agent is not necessarily required of course, so long as the conditions used do in fact achieve import.

Uses

INTRODUCING NON-NATURAL AMINO ACIDS INTO PROTEINS. As noted above, the inventive techniques and reagents may be used to introduce one or more unnatural amino acids into proteins. Any tRNA may be utilized, along with any unnatural amino acid. As will be appreciated by those of ordinary skill in the art, preferred embodiments of introducing unnatural amino acids into proteins utilize tRNAs that are aminoacylated prior to import into cells. Preferably, such tRNAs are not substrates for endogenous tRNA synthetases.

Introduction of unnatural amino acids into proteins or polypeptides in accordance with the present invention can be useful to probe the mechanical and/or functional characteristics of protein structure. For example, incorporation of detectable (e.g., fluorescent) moieties can allow the study of protein movement within and without cells. Alternatively or additionally, incorporation of reactive moieties (e.g., photoactivatable groups) can be used to identify interaction partners and/or to define three-dimensional structural motifs. Also, incorporation of amino acids such as phosphotyosive or phosphoserine, or analogs thereof, can be used to study cell signalling requirements.

In certain preferred embodiments, the inventive system may be utilized to introduce two or more different amino acid analogues into a single protein. Such multiple modifications can be used to dissect intra-protein interactions and to study protein folding and dynamics. For example, introduction of two different fluorescent groups in the same protein allows one to use fluorescence resonance energy transfer (FRET) to analyze the three-dimensional proximity of the labelled groups in the folded protein, and whether this, proximity changes during the lifetime or activity cycle of the protein.

Alternatively or additionally, the inventive system may be utilized to read through different stop codons in different proteins within the same mammalian cell. Optionally, a different amino acid (natural or unnatural) can be introduced for each different stop codon involved.

GENE THERAPY: Nonsense mutations are responsible for a significant number of human genetic disorders (see, for example, Atkinson et al., *Nuc. Acids Res.* 22:1327, 1994). To give but a few examples, β-thalessemia, Duchenne muscular dystrophy, xeroderma pigmentosum, Farconi's anemia, and cystic fibrosis can all be caused by nonsense mutations in identified genes. For instance, Duchenne muscular dystrophy is caused by the absence of dystrophin protein, which may result from a nonsense mutation within the coding region of the dystrophin gene. The present invention could allow the delivery of suppressor tRNAs that, whether acylated internally or externally, would read through the stop codon and produce some level of dystrophin protein, so that disease symptoms are alleviated.

In certain preferred embodiments of the rescue of stop codon mutations in genetic diseases, tRNAs that act as substrates for endogenous tRNA synthetases are utilized; such tRNAs can be aminoacylated in vivo so that, whether or not they are aminoacylated prior to being introduced into the cells, they may be used to read through the relevant stop codon multiple times.

EXAMPLES

Example 1

Import of Amber and Ochre Suppressor tRNAs into Mammalian Cells

Materials and Methods

GENERAL. Standard genetic techniques were used for cloning (Sambrook et al. *Molecular Cloning: A Laboratory Manual*, Cold Spring Harbor Press, Cold Spring Harbor, N.Y., Second Edition, 1989), *E. coli* strains DH5α (Hanahan *J. Mol. Biol.* 166:557, 1983) and XL1-Blue (Bullock et al., *BioTechniques* 5:376, 1987) were used for plasmid propagation and isolation. For transfection of mammalian cells, plasmid DNAs were purified using an EndoFree Plasmid Maxi kit (Qiagen). Oligonucleotides were from Genset Oligos and radiochemicals were from New England Nuclear.

PLASMIDS CARRYING REPORTER GENES. pRSVCAT and pRSVCATam27 and pRSVCAToc27, carrying amber and ochre mutations, respectively, at codon 27 of the chloramphenicol acetyltransferase (CAT) gene, have been described previously (Capone et al., *Mol. Cell. Biol.* 6:3059, 1986).

PLASMIDS CARRYING SUPPRESSOR TRNA GENES. The plasmid pRSVCAT/trnfM U2:A71/U35A36/G72 contains the gene for the amber suppressor derived from the *E. coli* tRNA$^{fMet}$ (Lee et al., *Proc. Natl. Acad. Sci. USA* 88:11378, 1991). An ochre suppressor was generated from this plasmid by mutation of C34 to U34 in the tRNA gene using the QuikChange mutagenesis protocol (Stratagene). The plasmid pcDNA1 (Invitrogen) contains the gene for the supF amber suppressor derived from *E. coli* tRNA$^{Tyr}_1$ (Goodman et al., *Nature (London)* 217:1019, 1968).

PURIFICATION OF SUPPRESSOR TRNAS. For purification of the amber suppressor tRNA derived from *E. coli* tRNA$^{fMet}$, total tRNA (597 A$_{260}$ units) was isolated by phenol extraction of cell pellet from a 2 L culture of *E. coli* B 105 cells (Mandal et al., *J. Bacteriol.* 174:7827, 1992) carrying the plasmid pRSVCAT/trnfM U2:A71/U35A36/G72 (Lee et al., *Proc. Natl. Acad. Sci. USA* 88:11378, 1991). The suppressor tRNA was purified by electrophoresis of 80 A$_{260}$ unit aliquots of the total tRNA on 12% non-denaturing polyacrylamide gels (0.15×20×40 cm) (Seong et al., *Proc. Natl. Acad. Sci. USA* 84:334, 1987). The purified tRNA was eluted from the gel with 10 mM Tris-HCl (pH 7.4) and concentrated by adsorption to a column of DEAE-cellulose followed by elution of the tRNA with 1 M NaCl and precipitation with ethanol. The same procedure was used for purification of the ochre suppressor tRNA.

supF tRNA (Goodman et al., *Nature (London)* 217:1019, 1968) was purified from *E. Coli* strain MC1061p3 carrying the plasmid pCDNA1. Total tRNA (1,000 A$_{260}$ units) isolated by phenol extraction of cell pellet from a 3 L culture was dissolved in 10 ml of buffer A [50 mM NaOAc (pH 4.5), 10 mM MgCl$_2$, and 1 M NaCl] and applied to a column (1.5×1.5 cm) of benzoylated and naphthoylated DEAE-cellulose (BND-cellulose) (Sigma) equilibrated with the same buffer. The column was then washed with 500 ml of the same buffer. The supF tRNA and wild type tRNA$^{Tyr}$ were eluted with a linear gradient (total volume 500 ml) from buffer A to buffer B [50 mM NaOAc (pH 4.5), 10 mM MgCl$_2$, 1 M NaCl and 20% ethanol]. The separation of supF tRNA from tRNA$^{Tyr}$ was monitored by acid urea gel electrophoresis of column fractions followed by RNA blot hybridization. Fractions containing supF tRNA free of tRNA$^{Tyr}$ were pooled.

The purity of all three suppressor tRNAs was greater than 85% as determined by assaying for amino acid acceptor activity and by polyacrylamide gel electrophoresis.

IN VITRO AMINOACYLATION AND ISOLATION OF AMINOACYL-TRNAS. The U2:A71/U35A36/G72 mutant tRNA$^{fMet}$ (1 A$_{260}$ unit) was aminoacylated with tyrosine in a buffer containing 30 mM Hepes-KOH (pH 7.5), 50 mM KCl, 8 mM MgCl$_2$, 2 mM DTT, 3 mM ATP, 0.4 mM tyrosine, 0.18 mg/ml BSA, 1 unit of inorganic pyrophosphatase and 20 µg of purified yeast TyrRS (Kowal et al., *Proc. Natl. Acad. Sci. USA* 98:2268, 2001) in a total volume of 0.4 ml. Aminoacylation of supF tRNA (1 A$_{260}$ unit) was performed in 50 mM Hepes-KOH (pH 7.5), 100 mM KCl, 10 mM MgCl$_2$, 5 mM DTT, 4 mM ATP, 25 µM tyrosine, 0.18 mg/ml BSA, 1 unit of inorganic pyrophosphatase and 20 units of purified *E. coli* TyrRS in a total volume of 0.4 ml. Reactions were incubated at 37° C. for 30 min, extracted with phenol equilibrated with 10 mM NaOAc (pH 4.5) and the concentration of NaOAc in the aqueous layer was raised to 0.3 M. The aminoacyl-tRNA was then precipitated with 2 volumes of ethanol. The tRNA was dialyzed against 5 mM NaOAc (pH 4.5), re-precipitated with ethanol, and dissolved in sterile water.

TRANSFECTION OF COS-1 CELLS. Cells were cultured in Dulbecco's modified Eagle's medium (DMEM with 4,500 mg/l glucose and 4 mM L-glutamine; Sigma) supplemented with 10% calf serum (Life Technologies), 50 U/ml penicillin and 50 µg/ml streptomycin (both Life Technologies) at 37° C. in a 5% CO$_2$ atmosphere. 18–24 hours before transfection, cells were subcultured in 12 well dishes (Ø 1.5 cm). Transfection reagent Effectene (Qiagen) was used according to the manufacturer's protocol. Briefly, cells at approximately 30% confluence were transfected with a mixture comprising 1.25 µg of plasmid DNA carrying the reporter gene and 0–5 µg of suppressor tRNA. The mixture of plasmid DNA and tRNA was diluted with EC buffer, supplied by the manufacturer, to a total volume of 50 µl, incubated for 5 min, then mixed with Enhancer (1 µl per µg of total nucleic acids) and incubated for a further 5 min. Effectene (2 µl per µg of total nucleic acids) was added, and the mixture was incubated for 10 min to allow for Effectene-nucleic acid complex formation. All steps above were carried out at room temperature (25° C.). The complexes were diluted with prewarmed (37° C.) DMEM to a total volume of 0.5 ml and added immediately to the cells. 1 ml of medium supplemented with serum and antibiotics was added 6 hours after transfection. Cells were harvested 24–30 hours post-transfection.

ASSAY FOR CAT ACTIVITY. Transfected cells were harvested by adding 0.5 ml of 140 mM NaCl, 20 mM Tris-HCl (pH 7.4), 10 mM EDTA. Cells were then pelleted by centrifugation, resuspended in 30 µl of 0.25 M Tris-HCl (pH 8.0), and lysed by multiple freeze-thaw-cycles. Lysates were clarified by centrifugation, and the protein concentration of the supernatants was determined (BCA protein assay; Pierce) using BSA as standard. 0.5–30 µg of total protein extract in a volume of 20 µl was incubated for 10 min at 65° C. and quick-chilled on ice. The standard reaction (50 µl) contained 20 µl extract, 0.64 mM acetyl coenzyme A, and 1.75 mmol of [$^{14}$C]-chloramphenicol (CAM) in 0.5 M Tris-HCl (pH 8.0). After 1 h at 37° C., the reaction was terminated by addition of ethyl acetate and mixing. The ethyl acetate layer was evaporated to dryness, dissolved in ethyl acetate (5 µl) and the solution was applied on to silica gel plates for chromatography with chloroform:methanol (95:5) as the solvent. Following autoradiography, radioactive spots were excised from the plate, and the radioactivity was quantitated by liquid scintillation counting.

ANALYSIS OF IN VIVO STATE OF TRNAS. Total RNAs were isolated from COS1 cells under acidic conditions using TRI-Reagent (Molecular Research Center). tRNAs were separated by acid urea polyacrylamide gel electrophoresis (Varshney et al., *J. Biol. Chem.* 266:24712, 1991) and detected by RNA blot hybridization using 5'-$^{32}$P-labeled oligonucleotides.

Results

IMPORT OF AMBER SUPPRESSOR TRNA INTO MAMMALIAN COS1 CELLS. The assay for import and function of the amber suppressor tRNA (FIG. 1) consisted of co-transfection of COS 1 cells with the suppressor tRNA along with the pRSVCATam27 DNA carrying an amber mutation at codon 27 of the chloramphenicol acetyltransferase (CAT) gene followed by measurement of CAT activity in cell extracts. The suppressor tRNA used (FIG. 2A) is derived from the *E. coli* initiator tRNA$^{fMet}$ and has mutations in the acceptor stem and the anticodon sequence. This tRNA is part of a 21$^{st}$ synthetase-tRNA pair that were developed previously for use in *E. coli* (Kowal et al., *Proc. Natl. Acad. Sci. USA* 98:2268, 2001). The G72 mutation in the acceptor stem allows it to act as an elongator tRNA and the U35A36 mutations in the anticodon sequence allow it to read the UAG codon (Seong et al., *J. Bio. Chem.* 264:6504, 1989). Because the suppressor tRNA contains the C1:G72 base pair, which is one of the critical determinants for eukaryotic TyrRSs, it is aminoacylated in vivo with tyrosine by yeast (Lee et al., *Proc. Natl. Acad. Sci. USA* 88:11378, 1991; Chow et al., *J. Bio. Chem.* 268:12855, 1993) and in vitro by human (Wakasugi et al., *EMBO J.* 17:297, 1998) and COS1 cell TyrRS and is, therefore, expected to be aminoacylated, at least to some extent, with tyrosine in mammalian cells. The tRNA is active in suppression of amber codons in yeast (Lee et al., *Proc. Natl. Acad. Sci. USA* 88:11378, 1991) and is, therefore, likely to be active in suppression of amber codons in mammalian cells. The tRNA was purified by electrophoresis on 12% polyacrylamide gels and used as such. The methods or reagents used for transfection included electroporation, DEAE-dextran, calcium phosphate, Superfect, Polyfect, Effectene, Lipofectamine, Oligofectamine, or DMRIE-C, a 1:1 (M/M) mixutre of 1,2-dimyristyloxypropyl-3-dimethyl-hydroxyethyl ammonium bromide with cholesterol. No CAT activity was detected in extracts of cells co-transfected using electroporation, DEAE-dextran, calcium phosphate, Superfect or Polyfect. Among the other reagents used, CAT activity was highest (by a factor of >25 fold compared to others) in extracts of cells co-transfected using Effectene (data not shown). The experiments described below for import and function of the suppressor tRNAs were, therefore, all carried out in the presence of Effectene.

Figure 3:
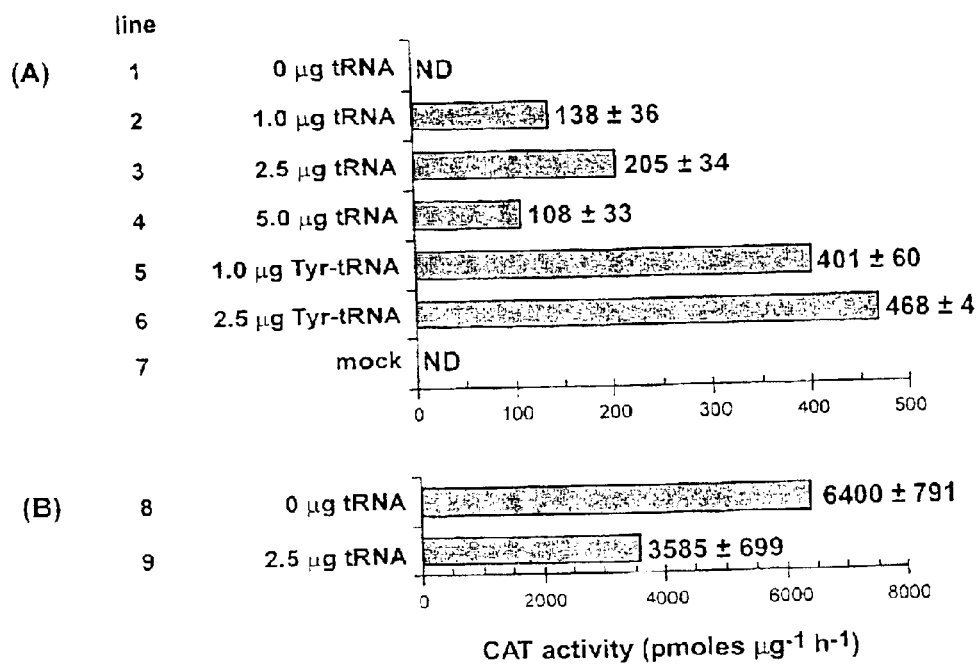
FIG. 3A shows CAT activity detected in extracts of cells co-transfected with the pRSVCATam27 DNA and varying amounts of amber suppressor tRNA, with or without aminoacylation.
FIG. 3B shows CAT activity detected in extracts of cells co-transfected with the wild type pRSVCAT DNA with or without the amber suppressor tRNA. The CAT activities are the average of three independent experiments. ND=not detectable.

FIG. 3A shows the results of assay for CAT activity in extracts of cells co-transfected with a fixed amount of the pRSVCATam27 plasmid DNA and varying amounts of the suppressor tRNA. Synthesis of CAT requires the presence of the suppressor tRNA during transfection (compare line 1 with lines 2–4). CAT activity reaches a maximum with 2.5 µg of the suppressor tRNA; with 5 µg of the suppressor tRNA, there is a substantial drop in CAT activity (FIG. 3A, lines 3 and 4). This drop in CAT activity is most likely due to an effect of the increased amount of the tRNA on efficiency of co-transfection of the plasmid DNA, since a similar effect of the tRNA is seen on co-transfection of the wild type plasmid DNA (FIG. 3B, lines 8 and 9). The CAT activity in extracts of cells transfected with 2.5 µg of the suppressor tRNA is about 6% of that in cells co-transfected with the wild type pRSVCAT plasmid and the same amount of the suppressor tRNA (FIGS. 3A and B, lines 3 and 9). This is most likely a reflection of the extent of aminoacylation of the suppressor tRNA, the efficiency of amber suppression at this site with the tRNA used and efficiencies of co-transfection of both the plasmid DNA and the suppressor tRNA into COS1 cells.

Figure 4:
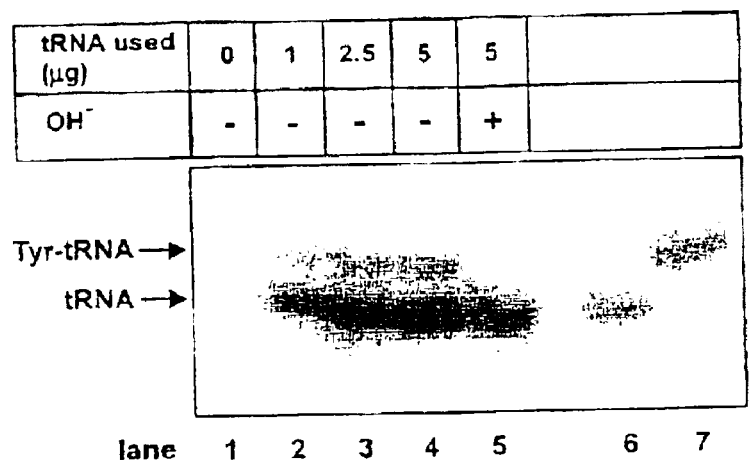
FIG. 4 shows acid urea gel analysis of tRNA isolated from cells co-transfected with pRSVCATam27 DNA and increasing amounts of the amber suppressor tRNA derived from the E. coli tRNA$^{fMet}$ (lanes 1–5). Lane 5 contains the same sample as lane 4 except that the aminoacyl linkage to the tRNA was hydrolyzed by base treatment (OH$^-$). Lanes 6 and 7 provide markers for tRNA and Tyr-tRNA, respectively.

Northern blot analysis shows that only about 8.6% of the suppressor tRNA is aminoacylated in COS1 cells (FIG. 4). Thus, aminoacylation of the tRNA is likely one of the factors limiting the extent of suppression of the amber mutation in the CAT gene. Further support for this comes from experiments described below using the ochre suppressor derived from the same tRNA and aminoacylated amber suppressor tRNA.

Figure 2:
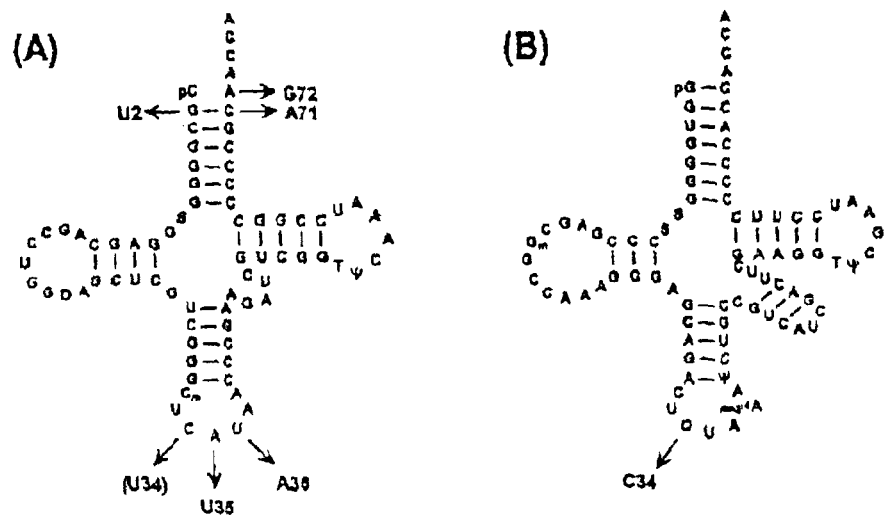
FIG. 2A (SEQ ID NO: 1) shows the cloverleaf structures of amber and ochre suppressor tRNAs derived from *E. coli* initiator tRNA$^{fMet}$. The ochre suppressor contains the U34 mutation (in parenthesis) in addition to the other mutations present in the amber suppressor tRNA.
FIG. 2B (SEQ ID NO: 2) shows the supF amber suppressor tRNA derived from *E. coil* tyrosine tRNA. Arrows indicate the sequence changes in the suppressor tRNAs.

IMPORT OF OCHRE SUPPRESSOR TRNA INTO COS1 CELLS. The amber suppressor tRNA described above was further mutated in the anticodon (C34 to U34) to generate an ochre suppressor tRNA (FIG. 2A). The import and function of the ochre suppressor tRNA was monitored by co-transfection of COS 1 cells with the suppressor tRNA and the pRSVCA-Toc27 plasmid DNA. Results of experiments carried out in parallel with the ochre and amber suppressor tRNAs show that the ochre suppressor tRNA is about 2-fold more active in suppression of the ochre codon than the amber suppressor tRNA is in suppression of the amber codon (Table 1). This is most likely due to the fact that the ochre suppressor tRNA is a better substrate for yeast and mammalian TyrRS than the amber suppressor tRNA. Both the amber and ochre suppressor tRNAs are specific in suppression of the corresponding codons (Table 1). These results appear, at the outset, to be consistent with the known specificity of amber and ochre suppressors in eukaryotes for the corresponding codons (Capone et al., *Mol. Cell. Biol.* 6:3059, 1986; Sherman et al. in *The Molecular Biology of the Yeast Saccharomyces—Metabolism and Gene Expression* (Strathern et al., Eds.), Cold Spring Harbor Laboratory Press, Cold Spring Harbor, N.Y., pp. 463–486, 1982). However, in *E. coli*, although amber suppressor tRNAs are known to be specific for amber codons, ochre suppressor tRNAs can also read amber codons (Brenner et al., *J. Mol. Biol.* 13:629, 1965; Eggertsson et al., *Microbiol. Rev.* 52:354, 1988). Therefore, the finding here that an ochre suppressor tRNA isolated from *E. coli* is specific for an ochre codon in a mammalian cell is surprising and should be further analyzed. Measurements of CAT activity shown on Table 1 were carried out using 2.5 µg of protein in the COS1 cell extracts. Use of ten fold more protein in the assay still failed to detect CAT activity in extracts from cells transfected with the ochre suppressor tRNA along with the pRSVCATam27 plasmid DNA.

IMPORT OF AMINOACYL-AMBER SUPPRESSOR TRNA INTO COS1 CELLS. The approach for site-specific insertion of amino acid analogues into proteins requires the import of suppressor tRNA aminoacylated with the amino acid analogue of choice into mammalian cells. In an attempt to determine whether the aminoacyl-linkage in aminoacyl-suppressor tRNA would survive the time and the conditions of transfection needed for import of the suppressor tRNA, the above experiments were repeated with the amber suppressor tRNA that had been previously aminoacylated with tyrosine using yeast TyrRS. Comparison of CAT activity in extracts of cells transfected with the amber suppressor tRNA to that in cells transfected with the amber suppressor Tyr-tRNA shows that at both concentrations of the tRNAs used, CAT activity was significantly higher (2–3 fold) in cells transfected with the Tyr-tRNA (FIG. 3A, compare lines 5 and 6 to lines 2 and 3, respectively). These results demonstrate that an aminoacylated amber suppressor tRNA can withstand the time and the conditions of transfection needed for import into COS1 cells and insert the amino acid attached to the tRNA to a growing polypeptide chain on the ribosome in response to an amber codon.

IMPORT OF E. COLI SUPF TRNA INTO COS1 CELLS. The approach for site-specific insertion of amino acid analogues into proteins in mammalian cells using the import of suppressor tRNA requires that the suppressor tRNA should not be a substrate for any of the mammalian aaRSs. Otherwise, once the suppressor tRNA has inserted the amino acid analogue at a specific site in the protein, it will be re-aminoacylated with one of the twenty normal amino acids and insert this normal amino acid at the same site. While the amber suppressor tRNA described above proved quite useful for the initial work in determining the conditions necessary for import of both the suppressor tRNA and the reporter plasmid DNA into mammalian cells, the tRNA is a substrate for mammalian TyrRS and is, therefore, not suitable for site-specific insertion of amino acid analogues into proteins in mammalian cells.

Figure 5:
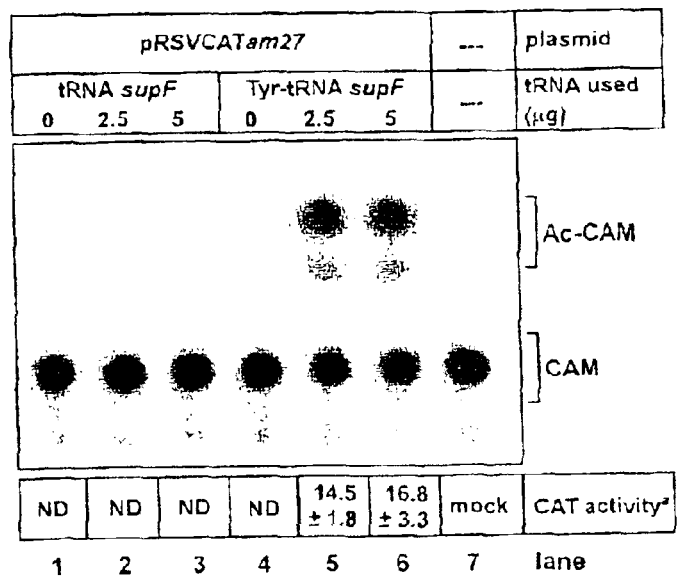
FIG. 5 shows results of thin layer chromatographic assay for CAT activity in extracts of COS1 cells transfected with pRSVCATam27 DNA (lanes 1 and 4) and supF tRNA, uncharged (lanes 2 and 3), or charged (lanes 5 and 6). Lane 7, mock transfected; CAM, unreacted substrate and Ac-CAM, the products formed. The CAT activities are the average of two independent experiments. ND, not detectable.

The tRNA selected for this purpose was the E. coli supF tRNA, the amber suppressor tRNA derived from the E. coli tRNA$^{Tyr}_1$ (FIG. 2B). This tRNA is not a substrate for yeast, rat liver or hog pancreas TyrRS (Clark et al., J. Biol. Chem. 237:3698, 1962; Doctor et al., J. Biol. Chem. 238:3677, 1963) or any of the yeast aaRSs (Edwards et al., Mol. Cell. Biol. 10:1633, 1990). It is also not a substrate for the COS1 cell TyrRS. The SupF tRNA was overproduced in E. coli, purified by column chromatography on BND-cellulose and was aminoacylated with tyrosine using E. coli TyrRS. The SupF tRNA or SupF Tyr-tRNA was co-transfected into COS1 cells along with the pRSVCATam27 plasmid DNA and cell extracts were assayed for CAT activity. Extracts of cells co-transfected with up to 5 µg of the supF tRNA had no CAT activity (FIG. 5, lanes 2 and 3). In contrast, extracts of cells co-transfected with the supF Tyr-tRNA had CAT activity (FIG. 5, lanes 5 and 6). These results provide the first indication that an approach involving the import of suppressor tRNA aminoacylated with an amino acid analogue can form the basis of a general method for the site-specific insertion of amino acid analogues into proteins in mammalian cells. The absence of any CAT activity in cells transfected with the supF tRNA shows that this tRNA is not a substrate for any of the mammalian aaRSs and fulfills the requirement described above for the suppressor tRNA to be used for import into mammalian cells.

OTHER EMBODIMENTS

Other embodiments of the invention will be apparent to those skilled in the art from a consideration of the specification or practice of the invention disclosed herein. It is intended that the specification and examples be considered as exemplary only, with the true scope and spirit of the invention being indicated by the following.

What is claimed is:

1. An isolated mammalian cell including a suppressor tRNA that was not synthesized by the cell.

2. The mammalian cell of claim 1, wherein the suppressor tRNA is not a substrate for any tRNA synthetase in the cell.

3. The mammalian cell of claim 1, wherein the tRNA was acylated prior to being introduced into the cell.

4. An isolated mammalian cell which synthesizes a polypeptide including at least one unnatural amino acid by read-thru of a nonsense codon by a tRNA that was not synthesized by a cell.

5. A method for synthesizing proteins in mammalian cells by translation of genes containing at least one stop codon within the open reading frame, the method comprising steps of:
   contacting an isolated mammalian cell with a suppressor tRNA that was not synthesized within the cell, so that the tRNA is taken up into the cell in a level sufficient to allow read-through of at least one stop codon in the cell.

6. The method of claim 5, wherein the step of contacting comprises:
   contacting the mammalian cell with an aminoacylated suppressor tRNA.

7. The method of claim 6, wherein the aminoacylated suppressor tRNA is aminoacylated with an unnatural amino acid.

8. A method for synthesizing proteins in mammalian cells by translation of genes containing at least two stop codons within the open reading frame, the method comprising steps of:
   providing an isolated mammalian cell containing at least one gene that includes at least two stop codons;
   contacting the cell with at least two different aminoacylated suppressor tRNAs so that the aminoacylated suppressor tRNAs are taken up into the cell at a level that allows read-through of the at least two stop codons.

9. The method of claim 8, wherein the step of contacting comprises contacting the mammalian cell with at least two aminoacylated suppressor tRNAs, at least one of which is amino acylated with an unnatural amino acid.

10. A method for synthesizing proteins in mammalian cells by translation of genes containing at least one stop codon within the open reading frame, the method comprising steps of:
   providing an isolated mammalian cell containing at least a first gene and a second gene, each of which includes at least one stop codon, wherein the stop codon(s) in the first gene and the second gene are of different types;
   contacting the cell with at least two different aminoacylated suppressor tRNAs so that the aminoacylated suppressor tRNAs are taken up into the cell at a level that allows read-through of the stop codons.

* * * * *

UNITED STATES PATENT AND TRADEMARK OFFICE
CERTIFICATE OF CORRECTION

PATENT NO. : 6,964,859 B2  Page 1 of 1
DATED : November 15, 2005
INVENTOR(S) : Rajbhandary, U. and Koehrer, C.

It is certified that error appears in the above-identified patent and that said Letters Patent is hereby corrected as shown below:

<u>Column 1,</u>
Line 9, insert the following heading and paragraph:
-- GOVERNMENT SUPPORT
This invention was made with government support under Grant Numbers GM17151 awarded by NIH, and DAAD19-99-1-0300 awarded by the Army. The government has certain rights in the invention. --.

Signed and Sealed this

Eighteenth Day of April, 2006

JON W. DUDAS
*Director of the United States Patent and Trademark Office*